United States Patent [19]

Baltz et al.

[11] 4,366,247
[45] Dec. 28, 1982

[54] PROCESS FOR PREPARING TYLACTONE

[75] Inventors: Richard H. Baltz, Indianapolis, Ind.; Eugene T. Seno, Norwich, England

[73] Assignee: Eli Lilly and Company, Indianapolis, Ind.

[21] Appl. No.: 162,977

[22] Filed: Jul. 2, 1980

[51] Int. Cl.³ .................... C12N 1/20; C12P 17/08
[52] U.S. Cl. ................... 435/124; 435/253; 435/896
[58] Field of Search ............. 435/117, 124, 119, 135, 435/148, 896, 253

[56] References Cited

U.S. PATENT DOCUMENTS

| | | | |
|---|---|---|---|
| 3,178,341 | 4/1965 | Hamill et al. | 435/896 |
| 3,326,759 | 6/1967 | Hamill et al. | |
| 3,344,024 | 9/1967 | Whaley et al. | |
| 3,459,853 | 8/1969 | Gorman et al. | 424/121 |
| 4,161,523 | 7/1979 | Weinstein et al. | 424/181 |
| 4,196,280 | 4/1980 | Umezawa et al. | 536/17 R |

FOREIGN PATENT DOCUMENTS 51-6037351 10/1976 Japan .
51-6037352 10/1976 Japan .

OTHER PUBLICATIONS

Suzuki et al., *Chemistry Letters*, 793–798 (1973).
Nash et al., Current Chemotherapy and Infectious Disease Proceedings of 11th ICC and the 19th ICAAC, American Soc. of Microbiol., 462–463 (1980).
Masamune et al., *J. Amer. Chem. Soc.*, 98(24), 7874–7875 (1976).
Nagel et al., *J. Org. Chem.*, 44(12), 2050–2052, (1979).
Grafe et al., *J. Antibiotics*, 33(6), 663–664 (1980).
Omura et al., Proceedings of the 100th Meeting of the Pharmaceutical Society of Japan, Mar. 10, 1980.
Kinumaki et al., *J. Antibiotics*, 30(6), 450–454 (1977).
Yamaguchi et al., *J. Antibiotics*, 31(5), 433–440 (1978).
Tsukiura et al., *J. Antibiotics*, 23(3), 89–99 (1969).

*Primary Examiner*—Esther M. Kepplinger
*Attorney, Agent, or Firm*—Nancy J. Harrison; Arthur R. Whale

[57] ABSTRACT

A process for preparing tylactone (20-dihydro-20,23-dideoxytylonolide), which has the formula:

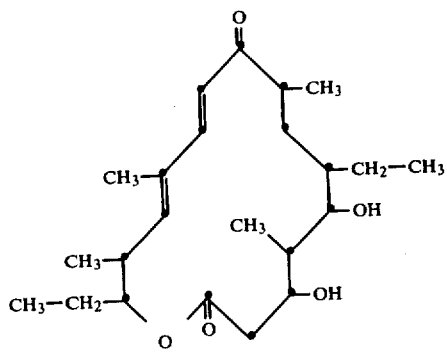

by submerged aerobic fermentation of *Streptomyces fradiae* NRRL 12188 or a tylactone-producing mutant or recombinant thereof is provided.

5 Claims, 1 Drawing Figure

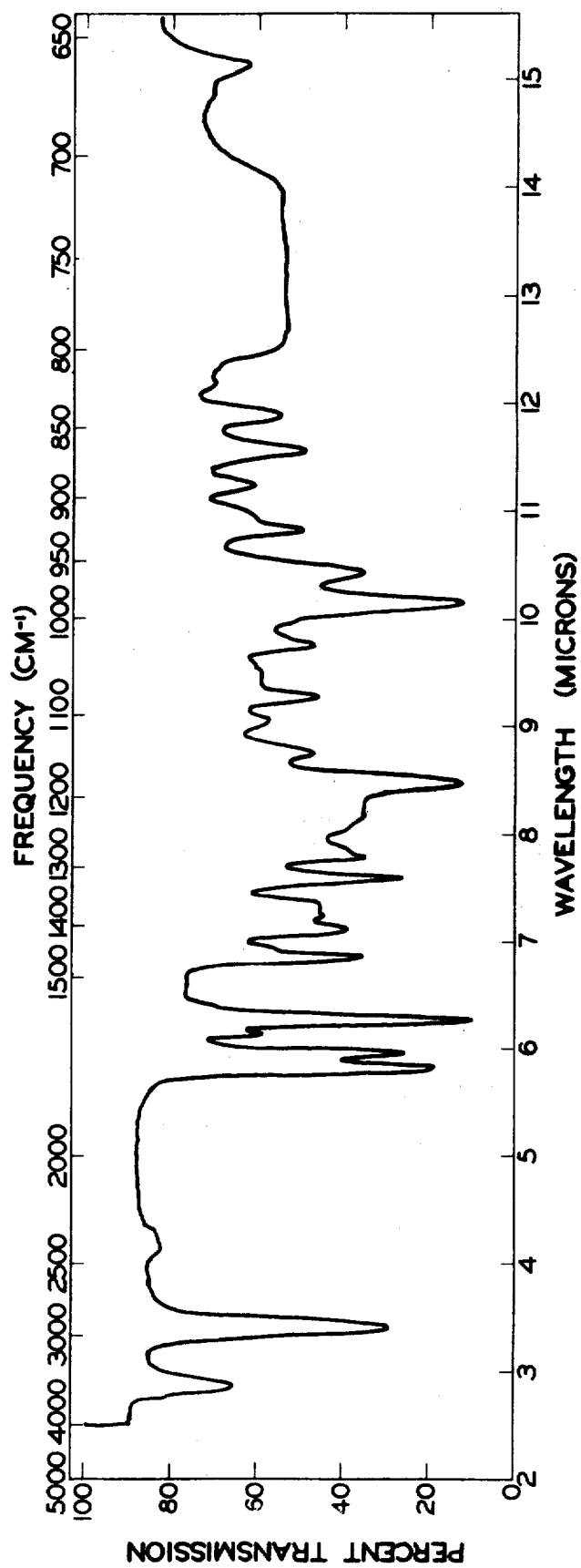

PROCESS FOR PREPARING TYLACTONE

SUMMARY OF THE INVENTION

This invention relates to a process for the preparation of a new macrolide compound. This new compound, which is 20-dihydro-20,23-dideoxytylonolide, will be called tylactone for convenience herein. Tylactone has structure 1:

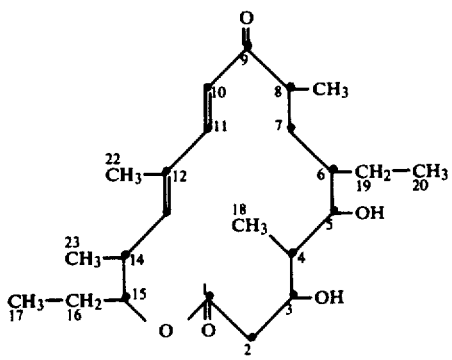

Tylactone is disclosed in a co-pending patent application by Robert L. Hamill, Gerald L. Huff, Richard H. Baltz and Eugene T. Seno entitled TYLACTONE, Ser. No. 162,976, filed herewith this even date.

Tylactone can be used to prepare related derivatives which have structure 2:

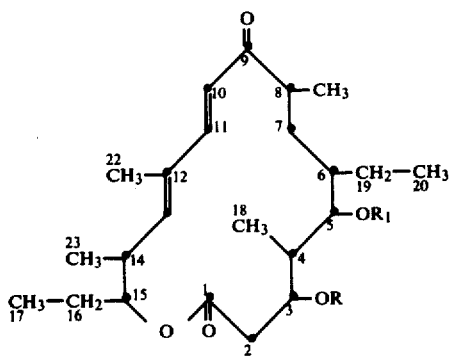

wherein R and $R_1$=an acyl moiety.

The compounds of structures 1 and 2 are useful intermediates from which 16-membered macrolide antibiotics can be prepared. Although no stereochemical assignments are indicated in the structures given herein, the stereochemistry of the compounds is identical to that of tylosin.

DESCRIPTION OF THE DRAWING

The infrared absorption spectrum of tylactone in chloroform is presented in the accompanying drawing.

DETAILED DESCRIPTION

The following paragraphs describe the properties of tylactone.

Tylactone

The structure of tylactone is shown in formula 1. Tylactone is a white solid which crystallizes from hexane or ethyl acetate-hexane and which melts at about 162°–163° C. It has the following approximate percentage elemental composition: carbon, 70%; hydrogen, 9.7%; oxygen, 20.3%. It has an empirical formula of $C_{23}H_{38}O_5$ and a molecular weight of about 394.

The infrared absorption spectrum of tylactone in chloroform is shown in the accompanying drawing. Observable absorption maxima occur at the following frequencies ($cm^{-1}$): 3534 (medium), 2924 (strong), 2398 (weak), 2353 (weak), 1709 (very strong), 1678 (very strong), 1626 (small), 1592 (very strong), 1458 (strong), 1441 (shoulder), 1404 (strong), 1379 (small), 1316 (strong), 1284 (medium), 1181 (very strong), 1143 (strong), 1103 (medium), 1078 (medium), 1049 (very small), 1025 (medium), 984 (very strong), 958 (strong), 923 (medium), 911 (shoulder), 859 (small), 868 (medium), 840 (medium), 820 (very small) and 661 (small).

The ultraviolet absorption (UV) spectrum of tylactone in neutral ethanol exhibits an absorption maximum at about 282 nm ($E_{1cm}^{1\%}=560$).

Tylactone has the following specific rotation: $[\alpha]_D^{25}-55.23°$(c 1, $CH_3OH$).

Electrometric titration of tylactone in 66% aqueous dimethylformamide indicates it has no titratable groups.

Tylactone is nearly insoluble in water, but is soluble in organic solvents such as acetone, methanol, ethanol, dimethylformamide, chloroform, diethyl ether, petroleum ether, benzene and dimethyl sulfoxide.

Tylactone can be distinguished from tylosin by silica-gel thin-layer chromatography. Sulfuric acid spray, either concentrated or dilute (50%), may be used for detection. With this detection system tylactone appears initially as a yellow-to-brown spot. If silica-gel plates with a fluorescent background are used in the chromatography, UV detection is convenient. The approximate Rf values of tylactone are summarized in Table 1.

TABLE 1

| Thin-Layer Chromatography of Tylactone[a] | | |
|---|---|---|
| | Rf Value | |
| Compound | A[b] | B |
| Tylactone | 0.50 | 0.62 |
| Tylosin | 0.0 | 0.0 |

[a]Medium: Silica gel
[b]Solvent: A = benzene: ethyl acetate (4:1) B = benzene: ethyl acetate (3:2)

Ester Derivatives

Tylactone can be esterified at the 3- and 5-hydroxyl groups to give acyl ester derivatives by treatment with acylating agents using methods known in the art. The acyl ester derivatives of tylactone are useful as intermediates in the preparation of new macrolide antibiotics.

Typical acylating agents include anhydrides, halides (usually in combination with a base or other acid scavenger) and active esters of organic acids. Acylation can also be achieved by using a mixture of an organic acid and a dehydrating agent such as N,N'-dicyclohexylcarbodiimide. Acylations can also be carried out enzymatically using procedures such as those described by Okamoto et al. in U.S. Pat. No. 4,092,473. Once formed, the acyl derivatives can be separated and purified by known techniques.

The derivatives can be prepared by esterification techniques generally known in the art, such as, for example, treatment of the compound with a stoichiometric quantity (or a slight excess) of an acylating agent, such as an acyl anhydride, in an organic solvent (for example, pyridine) at about 0° C. to about room temperature for from about 1 to about 24 hours until esterification is substantially complete. The ester derivative can be isolated from the reaction mixture by standard procedures such as extraction, chromatography and crystallization.

Useful esters are those of organic acids including aliphatic, cycloaliphatic, aryl, aralkyl, heterocyclic carboxylic, sulfonic and alkoxycarbonic acids of from 1 to 18 carbon atoms, and of inorganic acids, such as sulfuric and phosphoric acids.

Representative suitable esters include those derived from acids such as formic, acetic, chloroacetic, propionic, butyric, isovaleric, glucuronic, alkoxycarbonic, stearic, cyclopropanecarboxylic, cyclohexanecarboxylic, β-cyclohexylpropionic, 1-adamantanecarboxylic, benzoic, phenylacetic, phenoxyacetic, mandelic and 2-thienylacetic acids, and alkyl-, aryl-, and aralkyl-sulfonic acids, the aryl- and aralkyl- acids optionally bearing substituents such as halogen, nitro, lower alkoxy and the like on the aromatic moiety. Suitable esters also include hemiesters derived from dicarboxylic acids such as succinic, maleic, fumaric, malonic and phthalic acids.

Preparation of Tylactone

Tylcatone is prepared by culturing a strain of *Streptomyces fradiae* which produces these compounds under submerged aerobic conditions in a suitable culture medium until a substantial amount of the desired compound is produced.

The culture medium used to grow the *Streptomyces fradiae* can be any one of a number of media. For economy in production, optimal yield, and ease of product isolation, however, certain culture media are preferred. Thus, for example, preferred carbon sources in large-scale fermentation include carbohydrates such as dextrin, glucose, starch, and corn meal and oils such as soybean oil. Preferred nitrogen sources include corn meal, soybean meal, fish meal, amino acids and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of tylactone submerged aerobic fermentation in tanks is preferred. Small quantities of tylactone may be obtained by shake-flask culture. Because of the time lag in production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the vegetative inoculum can be the same as that used for larger fermentations, but other media can also be used.

The method of this invention comprises culturing a new microorganism which was obtained by chemical mutagenesis of a *Streptomyces fradiae* strain which produces tylosin. The new microorganism produces only minimal amounts of tylosin, but produces tylactone as a major component.

This invention also relates to the new microorganism which produces tylactone. The new microorganism is also classified as a strain of *Streptomyces fradiae*. A culture of this microorganism has been deposited and made part of the stock culture collection of the Northern Regional Research Center, Agricultural Research, North Central Region, 1815 North University Street, Peoria, Ill., 61604, from which it is available to the public under the accession number NRRL 12188.

As is the case with other organisms, the characteristics of *Streptomyces fradiae* NRRL 12188 are subject to variation. For example, recombinants, mutants or variants of the NRRL 12188 strain may be obtained by treatment with various known physical and chemical mutagens, such as ultraviolet light, X-rays, gamma rays, and N-methyl-N'-nitro-N-nitrosoguanidine. All natural and induced variants, mutants and recombinants of *Streptomyces fradiae* NRRL 12188 which retain the characteristic of tylactone production are a part of this invention.

*S. fradiae* NRRL 12188 can be grown at temperatures between about 10° and about 40° C. Optimum production of tylactone appears to occur at temperatures of about 28° C.

As is customary in aerobic submerged culture processes, sterile air is bubbled through the culture medium. For efficient antibiotic production the percent of air saturation for tank production should be about 30% or above (at 28° C. and one atmosphere of pressure).

Production of tylactone can be followed during the fermentation by testing samples of the broth, using high-performance liquid chromatography with a UV detection system [see, for example, J. H. Kennedy in *J. Chromatographic Science*, 16, 492-495 (1978)].

Following its production under submerged aerobic fermentation conditions, tylactone can be recovered from the fermentation medium by methods used in the fermentation art. Because of the limited solubility of tylactone in water, it may not be altogether soluble in the medium in which it is produced. Recovery of tylactone, therefore, can be accomplished by (1) extraction of the fermentation broth or (2) filtration of the fermentation broth and extraction of both the filtered broth and the mycelial cake. A variety of techniques may be used in the extraction processes. A preferred technique for purification of the filtered broth involves extracting the broth (generally without pH adjustment) with a suitable solvent such as amyl acetate or petroleum ether, concentrating the organic phase under vacuum to give crystals or an oil. If an oil is obtained, it may be purified by adsorption chromatography.

The compounds of structures 1 and 2 are useful intermediates from which 16-membered macrolide antibiotics can be prepared. For example, tylactone (1) can be bioconverted to tylosin by adding it to a growing culture of a bioconverting microorganism. The bioconverting microorganism can be a *Streptomyces fradiae* strain which either produces tylosin itself or is capable of producing tylosin except that it is blocked in tylactone formation.

A strain which is capable of producing tylosin except that it is blocked in tylactone formation can be obtained by treating a tylosin-producing strain with a mutagen and screening survivors for those which are unable to produce tylosin. Those survivors which are unable to produce tylosin are further screened to determine which strains are also unable to produce tylactone. These strains are identified by adding tylactone to small shake-flask cultures of the selected survivors to determine if they produce tylosin.

*Streptomyces fradiae* strains NRRL 2702 and NRRL 2703 are examples of Streptomyces strains which are capable of producing tylosin. A typical mutagen which may be used to obtain the selected strains is N-methyl-N'-nitro-nitrosoguanidine.

The compound of structure 1 is especially useful in the preparation of labeled compounds for metabolic studies. By labeling either the tylactone portion or the added sugar moieties, the metabolic pathway of tylosin can be ascertained.

In order to illustrate more fully the operation of this invention, the following examples are provided:

EXAMPLE 1

A. Shake-flask Fermentation of Tylactone

A lyophilized pellet of *Streptomyces fradiae* NRRL 12188 is dispersed in 1–2 ml of sterilized water. A portion of this solution (0.5 ml) is used to inoculate a vegetative medium (150 ml) having the following composition:

| Ingredient | Amount (%) |
|---|---|
| Corn steep liquor | 1.0 |
| Yeast extract | 0.5 |
| Soybean grits | 0.5 |
| CaCO$_3$ | 0.3 |
| Soybean oil (crude) | 0.45 |
| Deionized water | 97.25 |

Alternatively, a vegetative culture of *S. fradiae* NRRL 12188 preserved, in 1-ml volumes, in liquid nitrogen is rapidly thawed and used to inoculate the vegetative medium. The inoculated vegetative medium is incubated in a 500-ml Erlenmeyer flask at 29° C. for about 48 hours on a closed-box shaker at about 300 rpm.

This incubated vegetative medium (0.5 ml) is used to inoculate 7 ml of a production medium having the following composition:

| Ingredient | Amount (%) |
|---|---|
| Beet molasses | 2.0 |
| Corn meal | 1.5 |
| Fish meal | 0.9 |
| Corn gluten | 0.9 |
| NaCl | 0.1 |
| (NH$_4$)$_2$HPO$_4$ | 0.04 |
| CaCO$_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of Tylactone

In order to provide a larger volume of inoculum, 60 ml of incubated vegetative medium, prepared in a manner similar to that described in section A, is used to inoculate 38 L of a second-stage vegetative growth medium having the following composition:

| Ingredient | Amount (%) |
|---|---|
| Corn steep liquor | 1.0 |
| Soybean meal | 0.5 |
| Yeast extract | 0.5 |
| CaCO$_3$ | 0.3 |
| Soybean oil (crude) | 0.5 |
| Lecithin (crude) | 0.015 |
| Water | 97.185 |
| Adjust pH to 8.5 with 50% NaOH solution. | |

This second-stage vegetative medium is incubated in a 68-liter tank for about 47 hours at 29° C.

Incubated second-stage medium (4 L) thus prepared is used to inoculate 40 liters of sterile production medium having the following composition:

| Ingredient | Amount (%) |
|---|---|
| Fish meal | 0.92 |
| Corn meal | 1.57 |
| Corn gluten | 0.92 |
| CaCO$_3$ | 0.21 |
| (NH$_4$)$_2$HPO$_4$ | 0.04 |
| Soybean oil (crude) | 3.15 |
| Lecithin | 0.09 |
| Water | 90.90 |
| Adjust pH to 7.2 with 50% NaOH solution. | |

The inoculated production medium is allowed to ferment in a 68-liter tank for about 5 days at a temperature of 28° C. The fermentation medium is aerated with sterile air to keep the dissolved oxygen level between about 30% and 50% and is stirred with conventional agitators at about 300 rpm.

EXAMPLE 2

Isolation of Tylactone

Fermentation broth (1600 L), obtained as described in Example 1, is filtered using a filter aid (3% Hyflo Supercel, a diatomaceous earth, Johns Manville Corp.). The pH of the filtrate is adjusted to about 9 by the addition of 2% sodium hydroxide. The filtrate is extracted with amyl acetate (400 L). The amyl acetate extract (which has a high optical density reading at 282 nm but no antimicrobial activity) is concentrated under vacuum to give an oil. The oil is dissolved in benzene (5 L). The benzene solution is chromatographed over a 5.25-×36-in. silica-gel (Grace, grade 62, Davison Chemical Co.) column, packed with benzene. Elution is monitored by silica-gel thin-layer chromatography, using a benzene:ethyl acetate (3:2) solvent system and conc. sulfuric acid spray for detection. The column is first eluted with benzene to remove lipid substances, then with benzene:ethyl acetate (9:1) to separate and isolate tylactone. Fractions containing tylactone are combined and evaporated under vacuum. Tylactone is crystallized from benzene-hexane or hot hexane to give about 2 g, m.p. 162°–163° C.

EXAMPLE 3

3,5-Di-O-acetyltylactone

Tylactone (200 mg), prepared as described in Example 2, is dissolved in pyridine (4 ml). Acetic anhydride (4 ml) is added. The resulting mixture is allowed to stand at room temperature for 16 hours and then is concentrated to dryness under vacuum. Methanol (5 ml) is added to the residue; the solution is heated at 60° for ½ hour and then is concentrated under vacuum to give 3,5-di-O-acetyltylactone. This compound has an $R_f$ value of about 0.59 on silica-gel thin-layer chromatography in a benzene:ethyl acetate (4:1) solvent system. The $R_f$ of tylactone in this system is about 0.3.

EXAMPLES 4–7

3,5-Di-O-propionyltylactone, prepared according to the procedure of Example 3, but using propionic anhydride.

3,5-Di-O-isovaleryltylactone, prepared according to the procedure of Example 3, but using isovaleric anhydride.

3,5-Di-O-benzoyltylactone, prepared according to the procedure of Example 3, but using benzoic anhydride.

3,5-Di-O-(n-butyryl)tylactone, prepared according to the procedure of Example 3, but using n-butyric anhydride.

EXAMPLE 8

Preparation of Tylosin from Tylactone

A *Streptomyces fradiae* strain which formerly produced tylosin but which is blocked in macrolide ring closure is fermented according to the procedure described in Example 1, Section A, except that a temperature of 28° C. is used. Tylactone is added to the fermentation 48 hours after inoculation. The fermentation is then continued until a substantial amount of tylosin is produced, i.e. about three additional days. The presence of tylosin is determined by testing samples of the broth against organisms known to be sensitive to tylosin. One useful assay organism is *Staphylococcus aureus* ATCC 9144. Bioassay is conveniently performed by an automated turbidometric method, by thin-layer chromatography or by high-performance liquid chromatography with UV detection.

EXAMPLE 9

Tylactone is prepared by the method of Example 1 except that a labeled acetate, propionate or butyrate is incorporated into the fermentation medium. Labeled tylactone thus produced is used to prepare tylosin according to the procedure of Example 8. Tylosin labeled on the macrolide ring is thereby provided.

EXAMPLE 10

Tylactone, prepared by the method of Example 1, is used to prepare tylosin according to the method of Example 8 except that a labeled sugar moiety such as glucose is added to the second fermentation to provide tylosin which is labeled on the sugar moiety.

We claim:

1. A process for preparing tylactone, which has the formula:

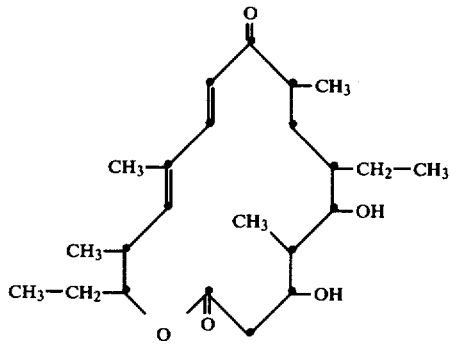

which comprises cultivating *Streptomyces fradiae* NRRL 12188 or a tylactone-producing mutant or recombinant thereof in a culture medium containing assimilable sources of carbon, nitrogen, and inorganic salts under submerged aerobic fermentation conditions until a substantial recoverable amount of compound is produced.

2. The method of claim 1 which comprises cultivating *Streptomyces fradiae* NRRL 12188.

3. The method of claims 1 or 2 which includes the additional step of isolating tylactone.

4. A biologically pure culture of the microorganism *Streptomyces fradiae* having the identifying characteristics of NRRL 12188 or a tylactone-producing mutant or recombinant thereof, said culture being capable of producing tylactone in a substantial recoverable quantity upon fermentation in a nutrient medium.

5. The culture of claim 4 wherein the microorganism is *Streptomyces fradiae* NRRL 12188.

* * * * *